(12) United States Patent
Schlosser et al.

(10) Patent No.: US 9,989,460 B2
(45) Date of Patent: Jun. 5, 2018

(54) SENSOR DEVICE FOR MONITORING THE STATE OF A LUBRICANT AND METHOD FOR PRODUCING SAID SENSOR DEVICE

(71) Applicants: SCHAEFFLER TECHNOLOGIES AG & CO. KG, Herzogenaurach (DE); AEMTEC GMBH, Berlin (DE)

(72) Inventors: Ingolf Schlosser, Eichwalde (DE); Martin Kram, Gerolzhofen (DE)

(73) Assignee: Schaeffler Technologies AG & Co. KG, Herzogenaurach (DE)

( * ) Notice: Subject to any disclaimer, the term of this patent is extended or adjusted under 35 U.S.C. 154(b) by 171 days.

(21) Appl. No.: 15/022,071

(22) PCT Filed: Jul. 25, 2014

(86) PCT No.: PCT/EP2014/066005
§ 371 (c)(1),
(2) Date: Mar. 15, 2016

(87) PCT Pub. No.: WO2015/039792
PCT Pub. Date: Mar. 26, 2015

(65) Prior Publication Data
US 2016/0223459 A1    Aug. 4, 2016

(30) Foreign Application Priority Data
Sep. 19, 2013    (DE) .......................... 10 2013 110 320

(51) Int. Cl.
*H01J 40/14*    (2006.01)
*G01N 21/47*    (2006.01)
(Continued)

(52) U.S. Cl.
CPC ....... *G01N 21/4738* (2013.01); *G01N 21/474* (2013.01); *G01N 21/55* (2013.01);
(Continued)

(58) Field of Classification Search
CPC ........................ F16N 2250/34; G01N 33/2888
See application file for complete search history.

(56) References Cited

U.S. PATENT DOCUMENTS

| 7,172,903 B2 | 2/2007 | Schilowitz et al. |
| 8,624,191 B2 | 1/2014 | Franke et al. |

(Continued)

FOREIGN PATENT DOCUMENTS

| CN | 1230922 | 12/2005 |
| DE | 2142179 | 3/1973 |

(Continued)

*Primary Examiner* — Thanh Luu
(74) *Attorney, Agent, or Firm* — Volpe and Koenig, P.C.

(57) ABSTRACT

Rolling bearings include a plurality of rolling bodies which during operation roll on raceways. In order to reduce friction during rolling, it is customary to supply the rolling bearings with a lubricant. However, the quality of the lubricant can deteriorate during operation due to long-term stress, aging, or thermal influences, or get lost in gaps etc. The objective addressed by the invention is that of providing a sensor device, which can be operated in a functionally reliable manner. This objective is achieved by a sensor device for monitoring the state of a lubricant in a lubricant chamber, including a transmitter platform, wherein on the transmitter platform, a plurality of diode devices are arranged, having a measurement window device, wherein the measurement window device is arranged between a measuring chamber and the lubricant chamber, having a receiving device, wherein at least one of the diode devices comprises a die and a plastic dome. The plastic dome and the die are connected by way of a contact surface, wherein the contact surface is arranged on an upper side of the die.

17 Claims, 4 Drawing Sheets

(51) Int. Cl.
*G01N 33/28* (2006.01)
*G01N 21/85* (2006.01)
*G01N 21/55* (2014.01)
*G01N 21/31* (2006.01)
*G01N 21/3577* (2014.01)
*G01N 21/552* (2014.01)
*H01L 25/16* (2006.01)
*H01L 33/54* (2010.01)

(52) U.S. Cl.
CPC ..... *G01N 21/8507* (2013.01); *G01N 33/2888* (2013.01); *F16N 2250/34* (2013.01); *G01N 21/314* (2013.01); *G01N 21/3577* (2013.01); *G01N 21/552* (2013.01); *G01N 2021/4769* (2013.01); *G01N 2201/062* (2013.01); *G01N 2201/068* (2013.01); *G01N 2201/0638* (2013.01); *H01L 25/167* (2013.01); *H01L 33/54* (2013.01); *H01L 2224/48091* (2013.01); *H01L 2224/8592* (2013.01)

(56) References Cited

U.S. PATENT DOCUMENTS

| | | | |
|---|---|---|---|
| 2002/0163006 | A1 | 11/2002 | Yoganandan et al. |
| 2009/0315057 | A1* | 12/2009 | Konishi .............. H01L 24/97 257/98 |
| 2010/0314377 | A1 | 12/2010 | Kasai et al. |
| 2013/0075616 | A1 | 3/2013 | Kram et al. |
| 2013/0241393 | A1* | 9/2013 | Hayashida ......... H01L 25/0753 313/502 |
| 2013/0250281 | A1* | 9/2013 | Shirata ............... G01N 33/2888 356/70 |

FOREIGN PATENT DOCUMENTS

| | | |
|---|---|---|
| DE | 102010005057 | 7/2011 |
| DE | 102010015084 | 10/2011 |
| DE | 102010031919 | 1/2012 |
| EP | 2445021 | 4/2012 |
| WO | 2009030202 | 3/2009 |

* cited by examiner

SENSOR DEVICE FOR MONITORING THE STATE OF A LUBRICANT AND METHOD FOR PRODUCING SAID SENSOR DEVICE

FIELD OF THE INVENTION

The invention relates to a sensor device for monitoring the state of a lubricant in a lubricant chamber. The invention also relates to a method for producing the sensor device.

BACKGROUND

Rolling bearings comprise a plurality of rolling bodies that roll on raceways during operation. To reduce the friction during rolling, it is typical to provide the rolling bearing with a lubricant. However, during operation, the quality of the lubricant can degrade due to long-term loading, aging, or thermal effects, or the lubricant can be lost due to cracks, etc. A consequence of degraded lubricant or reduced quantity of lubricant is that the friction in the rolling bearing increases and therefore, among other things, the service life of the rolling bearing is shortened.

In publication WO 2009/030202 A1, a measurement device and a method for analyzing the lubricant of a rolling bearing is presented. The measurement device comprises a plurality of transmitter diodes that transmit light in the near-infrared range onto a measurement location behind a measurement window that is in contact with the lubricant. The measurement device further comprises a receiving device that receives the reflected light of the transmitter diodes. Because certain wavelength ranges are significant for the quality states of the lubricant, by evaluating a spectrum of the light reflected from the measurement location, a conclusion can be made on the quality and/or quantity of lubricant in the rolling bearing.

The publication DE 10 2010 015 084 A1 that forms the closest prior art relates to a sensor part for an infrared sensor and to a method for its production. The sensor part is used, e.g., for use in the measurement device of the above publication. The sensor part comprises a contoured printed circuit board, wherein the sensor diodes are constructed as so-called DIEs. The sensor part is held in a sleeve that is filled with a gel of a silicon basis that is transparent to IR radiation and thus to the measurement radiation, so that, first, the opposing position of the transmitter diodes and the receiving device no longer changes, second, oxygen and water vapor are displaced, and third, the optical transition between the transmitter diodes built as DIEs to the environment is improved.

SUMMARY

The invention is based on objective of providing a sensor device that can be operated in a functionally reliable and correct manner with advantageous production. The invention is also based on the objective of providing a method for producing the sensor device. These and other objects are achieved by a sensor device and by a method with one or more features of the invention. Preferred or advantageous embodiments of the invention are given from the dependent claims, the following description, and the accompanying figures.

In the scope of the invention, a sensor device is provided that is suitable and/or constructed for monitoring the state of a lubricant in a lubricant chamber. In particular, the sensor device is constructed to detect state changes of the lubricant, in particular, the lubricating grease. The sensor device can monitor, in particular, the water content, turbidity, thermal and/or mechanical wear, and/or temperature of the lubricant. In particular, the spectrum in the NIR (near infrared range) and/or the MIR (mid-infrared range) is used as the measurement radiation for monitoring. One possible measurement method is described in the publication WO 2009/030202 A1 specified above, whose disclosure with reference to the measurement method is incorporated by reference in this text.

The sensor device comprises a transmitter platform, wherein a plurality of diode devices is arranged as transmitter devices for a measurement radiation on the transmitter platform. The transmitter platform is constructed, in particular, as a section of a circuit board. The diode devices are constructed to transmit measurement radiation in the NIR and/or MIR range. In an especially preferred way, at least two different diode devices are provided as transmitter devices, wherein the different diode devices differ by the spectrum of the emitted measurement radiation. The transmitter platform is arranged in a measurement chamber of the sensor device.

The sensor device further comprises a measurement window device that forms a transition from the measurement chamber into the lubricant chamber. The measurement window device can be constructed, for example, as a glass plate, in particular, as a sapphire glass plate. During operation it is especially preferred that the measurement window device has direct and/or body contact with the lubricant in the lubricant chamber.

Furthermore, the sensor device has at least one receiving device, e.g., a receiver diode, which is also arranged in the measurement chamber and is constructed for receiving measurement radiation that has been reflected from the measurement window device. During operation, the measurement radiation is emitted by the transmitter devices in the direction of the measurement window device. There, the measurement radiation is scattered and/or reflected, wherein the spectrum and/or the intensity of the measurement radiation is changed by the influence of the lubricant bordering the measurement window device as a function of the state of the lubricant. By monitoring the change of the spectrum and/or the intensity of the measurement radiation, a conclusion can be reached on the state of the lubricant. For example, a conclusion on the state of the lubricant can be reached through a ratio of the reflected measurement radiation of the transmitter devices with the first spectrum and the reflected measurement radiation of the transmitter devices with the second spectrum.

At least one of the diode devices, preferably a few and, in particular, all diode devices that are constructed as transmitter devices comprise—optionally each—a so-called DIE. The DIE is, in semiconductor engineering, the designation of a single, unhoused semiconductor chip. It can also be called a "bare chip." It is typically obtained by sawing or breaking the finished wafer into rectangular pieces (dicing), wherein a complete and functional component is located on each piece. In general usage, dicing means "cubes," but because the wafers are very thin, the DIEs do not look like cubes, but instead their shape corresponds preferably to flat square blocks. In particular, the diode devices are constructed as "bare chips" or "bare dies." The at least one diode device is realized especially with no housing.

In the scope of the invention it is provided that the sensor device has at least one dome, wherein the dome is placed on the at least one diode device and wherein the dome and the DIE are connected by a contact surface. The contact surface is arranged on a top side of the DIE, wherein a light-emitting diode area of the diode device is arranged on the same top side. In particular, the dome is connected to the DIE exclusively by the contact surface on the top side of the DIE.

The advantage of the invention is to be seen in that, by use of the dome with a very narrow construction in the width extent, a very high packing density or a very large spacing of the diode devices relative to each other can be achieved. This intermediate space between the diode devices is necessary, because it is required by tools for wire bond contacting and thus for wire bond tools. Furthermore, the attachment of the dome has the advantage that heat transfer from the diode device in the lateral direction toward the diode device is not prevented by the dome. The dome takes over the function of adapting the index of refraction of the diode device to the environment. Thus, filling the sensor device with fluid can be eliminated for this function. In particular, the sensor device is provided in the measurement chamber with an air atmosphere. In this way, the sensor device becomes more resistant to aging and therefore more reliable—in comparison with the prior art. In addition, thermal problems for the heating of the fluid are eliminated, so that the functionality of the sensor device is improved.

In one preferred construction of the invention, the dome is constructed with a drop-like shape on a flat surface and/or with a hemispherical shape with a flattened bottom surface, wherein the bottom surface of the dome forms the contact surface to the DIE. Through this shape, on one hand, the dome can be deposited in its original form, in particular, fluid form, wherein the shape of the dome is formed by the surface tension itself, so that no other shaping processes for the dome are required. On the other hand, in this construction the dome forms a converging lens, so that the measurement radiation is focused and/or bundled in the direction of the measurement window device.

In one preferred construction of the invention, the DIE has a substrate with side surfaces or is constructed as this substrate, wherein outer edges are formed between the side surfaces and the top side and wherein the contact surface is bounded on the top side of the DIE and thus of the substrate and is bordered by the side surfaces. In particular, the outer edges between the top side and the side surfaces form flow blocks for the casting in the production of the dome by deposition in fluid form as casting. Due to the bordering of the dome by the outer edges of the top side, the contact surface is reduced or limited as a flat base surface of the dome and forms a dome with a small radius of curvature and thus with large optical index of refraction due to the surface tension of the casting mass. In this construction, in addition to the low installation space requirements of the diode device, the optical damping of the measurement radiation in its passage through the dome is kept low.

In one preferred structural design, the transmitter platform is constructed as a circuit board, wherein the DIE is fixed on the circuit board, e.g., by adhesion, and is electrically connected to the circuit board with wires via wire bonds. In one preferred construction of the invention, the connection areas of at least one wire are arranged on the contact surface for the wire bonds, so that the dome fixes the wire, in addition to the optical effect, so that the functional security is increased. This structural design also reflects a preferred construction of the method for producing the sensor device, wherein initially the DIE is mounted on the circuit board, is then connected to the circuit board by means of wire bonds, and the dome is placed after the wire bonds.

In one preferred structural design, the sensor device has, in particular, a cylindrical housing section, wherein the measurement chamber is arranged with the transmitter devices and the at least one receiving device in the measurement chamber. The measurement chamber is constructed as an inner space of the housing section. The measurement window device closes the housing section at a free end.

In one preferred improvement of the invention, the sensor device has a plug-in housing, in particular, a pin-like plug-in housing, wherein the plug-in housing comprises the housing section. In particular, the housing section forms a part of the plug-in housing. Optionally and additionally, the transmitter platform can be housed with the transmitter devices and/or the at least one receiving device in a capsule or in a stand setup in the housing section, in order to be able to fix the mechanical positioning of the transmitter and receiving devices relative to each other. The plug-in housing advantageously has a maximum diameter of less than 10 mm and in particular less than 6 mm. Consequently, the transmitter platform is also constructed with a maximum diameter less than 10 mm, in particular, less than 6 mm. This improvement again underscores the requirement that the transmitter devices must have very small designs so that they can be integrated into the sensor device.

It is preferred that at least two, advantageously at least or exactly four or six diode devices are arranged on the transmitter platform. Advantageously, the diode devices are to be divided into two groups of diode devices that differ with respect to the spectrum of the emitted measurement radiation. During operation it is possible that the two groups of diode devices are operated alternating with each other, so that the at least one receiving device receives the modified spectrum of the first measurement radiation and subsequently the modified spectrum of the second measurement radiation as reflected measurement radiation from the measurement window device. Advantageously, each of the groups has three diode devices, so that the measurement window device can be illuminated uniformly or homogeneously.

In one preferred structural realization of the invention, the or another receiving device is arranged on the transmitter platform. The other receiving device can be constructed as a reference receiving device in order to be able to compensate for effects caused by aging or soiling of the diode device in the measurement evaluation. Through the integration of the or another receiving device on the transmitter platform, the space on the transmitter platform is further reduced, so that the requirements for miniature diode devices are increased.

In an especially preferred way, the transmitter platform forms a partial area of a flexible circuit board, wherein the flexible circuit board also has a receiver platform that is arranged parallel offset to the transmitter platform in the mounted state in the direction of the optical axis of the sensor device. The connection between the transmitter platform and receiver platform is given by additional partial areas of the flexible circuit board. In this way, a sensor part for the sensor device can be produced from a flexible circuit board, wherein this part carries both the transmitter devices and also the receiving devices.

A further subject of the invention relates to a method for producing the sensor device, as previously described or according to one of the preceding claims, wherein in a first step, the DIE or the DIEs of the at least one diode device are placed on the transmitter platform and connected to the transmitter platform and wherein in a subsequent step, the dome is placed on the DIE. In particular, the dome is deposited on the DIE as a casting compound. The casting compound and thus the material of the dome can be, for example, a plastic, in particular, a UV-curing plastic. Alternatively, a resin can also be used.

Through the later deposition of the dome in the form of a fluid material, it is achieved that the space requirements for the diode devices are minimized for installation, because the dome is placed only at a later time. Advantageously, between the placement, in particular, fixing of the diode device on the transmitter platform and the deposition of the dome, the diode device is electrically contacted by means of wire bonds to the transmitter platform constructed as a circuit board. The wire bonds are, in particular, thermal-compression bonds (TC bonds), thermosonic ball-wedge bonds (TS bonds), or ultrasonic wedge-wedge bonds (US bonds). For the wire bonds, at least one wire is bonded, on one side, to a diode contact position of the diode device and, on the other side, to a transmitter contact position of the transmitter platform, in particular, the circuit board. The diode contact position is covered, in an especially preferred way, by the dome or encased by the casting compound. Advantageously, the wire to the bonds has a diameter less than 50 µm.

BRIEF DESCRIPTION OF THE DRAWINGS

Other features, advantages, and effects of the invention result from the following description of a preferred embodiment of the invention and the accompanying figures. Shown herein are.

DETAILED DESCRIPTION OF THE PREFERRED EMBODIMENTS

Figure 1:
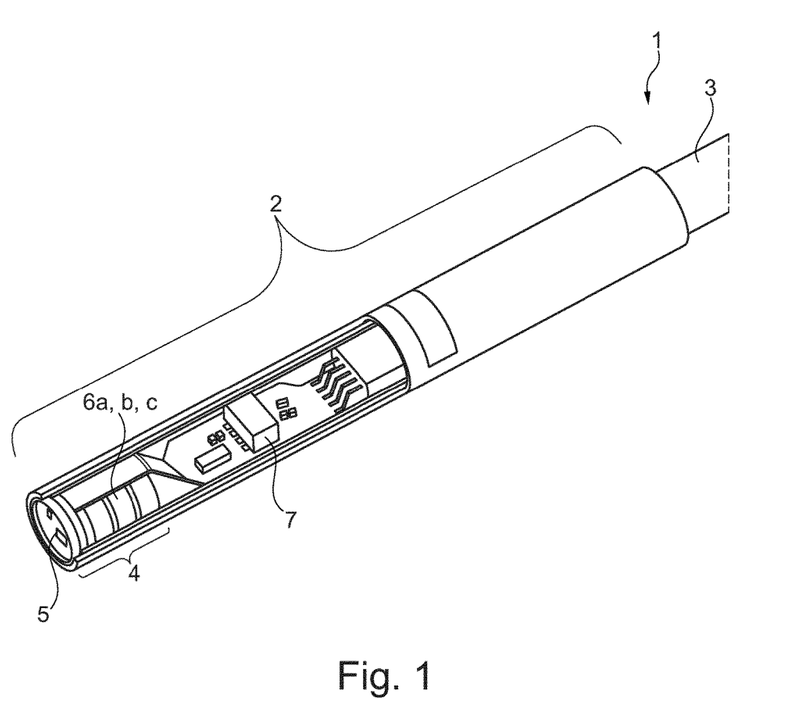
FIG. 1, a schematic three-dimensional representation of a sensor device as an embodiment of the invention, FIG. 2, a schematic representation of the measurement principle of the sensor device in FIG. 1, FIG. 3, a schematic three-dimensional representation of a sensor part of the sensor device in the preceding figures, FIG. 4, a schematic side plan view of a diode device of the sensor device of the preceding figures.

FIG. 1 shows, in a schematic three-dimensional representation, a sensor device 1 for monitoring the state of a lubricant in a lubricant chamber as an embodiment of the invention.

The sensor device 1 comprises a plug-in housing 2 that is provided on one end with a cable 3 for transmitting signals and for supplying power. The plug-in housing 2 has, for example, an outer diameter of 5 mm and a length of 40 mm, so that the sensor device is realized as a miniature sensor. The plug-in housing 2 is inserted with its free end into a lubricant chamber, so that the free end makes physical contact with the lubricant in the lubricant chamber. For example, the plug-in housing 2 can be used for monitoring lubricating grease in a rolling bearing, e.g., a large rolling bearing, wherein the plug-in housing 2 is positioned through an opening in the rolling bearing with its free end in or on the rolling body chamber with the lubricating grease.

The design as a miniature sensor has the advantage that the sensor device 1 can be arranged without large structural expense at almost any position of a device containing lubricant.

The free end of the sensor device 1 forms a housing section 4 that is closed on its end side with a measurement window device 5. In the housing section 4, a measurement capsule is built from individual rings 6a, b, c, which form spacing and stabilizing rings, arranged adjacent to the measurement window device 5. An evaluation device 7 that takes over the local power supply and the processing or pre-processing of signals in the sensor device 1 then attaches to the plug-in housing 2.

Figure 2:
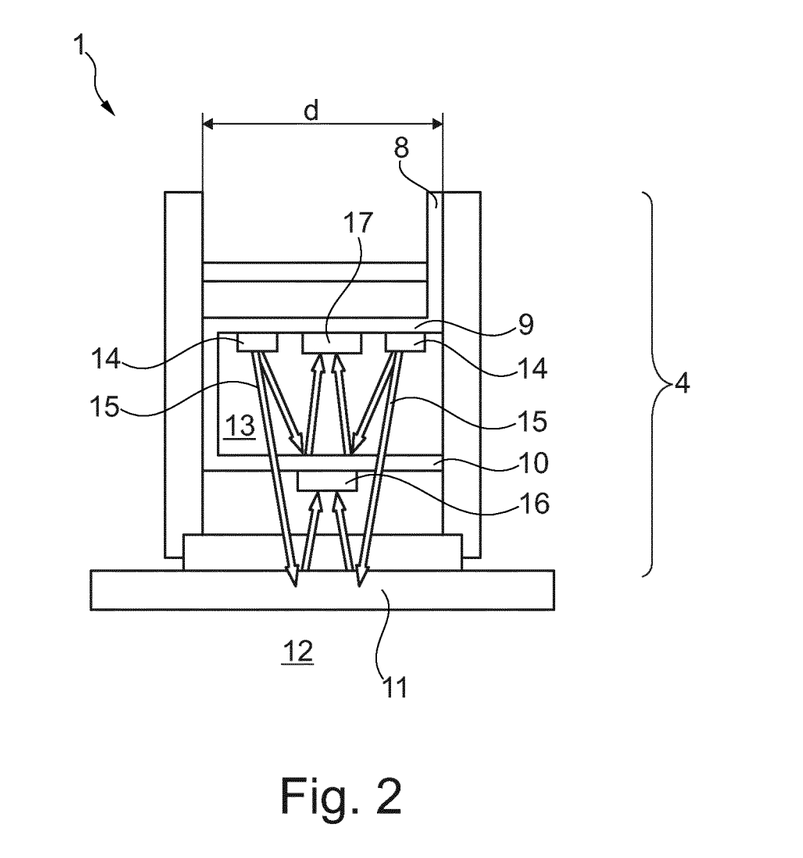

In FIG. 2, a schematic representation of the sensor device 1 is shown in the area of the housing section 4, in order to describe the measurement method. In the housing section 4 there is a circuit board 8 that comprises a transmitter platform 9 and a receiver platform 10. The transmitter platform 9 and the receiver platform 10 are oriented perpendicular to the longitudinal extent of the plug-in housing 2. As produced from the following figure, the receiver platform 10 does not cover the full surface, so that the measurement window device 5 is covered by the receiver platform 10 only in some sections. The housing section 4 is closed by the measurement window device 5 that is made from sapphire glass. During operation, the measurement window device 5 contacts a lubricant 11 in a lubricant chamber 12. The circuit board 8 with the transmitter platform 9 and the receiver platform 10 is arranged, in contrast, in a measurement chamber 13, wherein the lubricant chamber 12 and measurement chamber 13 are separated from each other by the measurement window device 5.

On the transmitter platform 9 there is a plurality of diode devices 14 that can emit a measurement radiation 15. The diode devices 14 are oriented so that these transmit the measurement radiation 15 in the direction of the measurement window device 5 and thus in the direction of the lubricant 11. On the receiver platform 10 there is a receiving device 16 as a measurement detector that is oriented so that it can receive measurement radiation 15 reflected by the measurement window device 5. The reflection of the measurement radiation 15 results, on one hand, due to a reflection of the measurement radiation 15 by the lubricant 11 or by the measurement window device 5. On the other hand, the reflected measurement radiation 15 involves diffusely scattered measurement radiation 15. A part of the measurement radiation 15 coming from the diode devices 14 is scattered or reflected directly on the bottom side of the receiver platform 10 and reflected into another receiving device 17 that is arranged on the transmitter platform 9 between the diode devices 14 and acts as a reference detector. The inner diameter d in the shown housing section 4 is 4.0 mm.

The diode devices 14 emit the measurement radiation 15 in different wavelength ranges and are activated, for example, alternating with each other. Through a comparison of the intensity of the measurement radiation 15 reflected by the lubricant 11, a conclusion can be made on the absorption of certain spectral ranges in the measurement radiation 15 and thus on the state of the lubricant 11.

Figure 3:
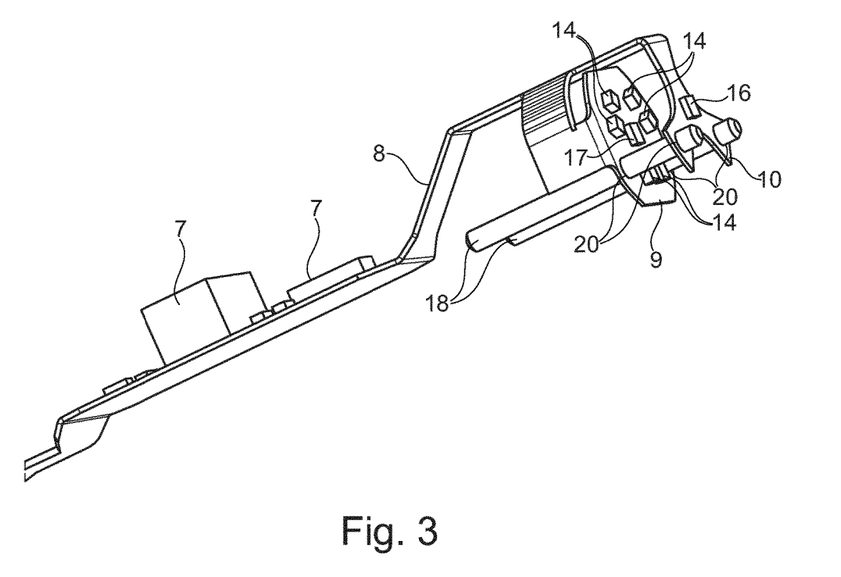

FIG. 3 shows the circuit board 8 as a sensor part in a schematic three-dimensional representation. It is to be seen that the circuit board 8 has a one-piece construction. The transmitter platform 9 has a nearly round circular construction; the receiver platform 10, in contrast, has a tri-axial design, wherein each axis has a v-shaped construction. The transmitter platform 9 and receiver platform 10 each have passage openings 20 that are aligned with each other congruently and each have pins 18, so that their relative position to each other is fixed. The individual rings 6a, b, c are also set in a line on the pins 18.

On the transmitter platform 9 there are, in total, six diode devices 14 that are positioned, however, so that these are not covered by the receiver platform 10 in the direction of the measurement window device 5.

As given from FIG. 3, the electronic components, namely the diode devices 14 and the other receiving device 17, are positioned very closely to each other. In order, nevertheless, to have sufficient space for the plurality of diode devices 14, the diode devices 14 are built as shown schematically in FIG. 4.

Figure 4:
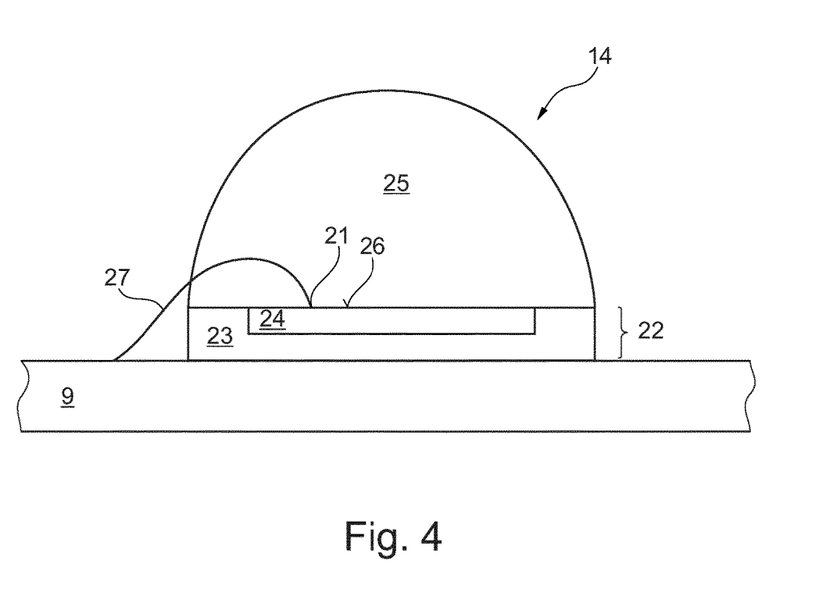

FIG. 4 shows a detail cutout in side view of the transmitter platform 9 with a diode device 14. The diode device 14 comprises a so-called DIE 22, that is, a block-shaped piece of a wafer. The DIE 22 comprises a substrate 23 in which the light-emitting diode area 24 is arranged. The diode area 24 is constructed, for example, as a p area.

The transition from the DIE 22 to the ambient air in the measurement chamber 13 is critical due to the large difference in the index of refraction between the DIE 22 and the ambient air. For this reason, a dome 25 is placed on the DIE 22, wherein the dome 25 is arranged with its entire contact surface 26 on a light-emitting top side of the DIE 22. The dome 25 is produced on the DIE 22 by depositing fluid plastic that is, e.g., UV-curable. For the deposition, a hemispherical shape of the dome 25 is automatically produced, so that the dome 25 is formed simultaneously as a collecting or focusing lens for the measurement radiation 15 that is emitted by the DIE 22 or by the diode area 24.

For the production of the sensor device 1, initially the circuit board 8 is equipped with the DIEs 22, e.g., in a flat state in a first step and then bonded to the circuit board 8 by means of wires 27. The wires 27 have a diameter less than 50 µm, so that the contacting can be realized in a way that saves a lot of installation space. In a subsequent step, casting compound is deposited and cured on the top side of the DIE 22, so that the dome 25 is formed. The casting compound also surrounds, in particular, at least one diode contact point 21 of the diode area 24, so that this is mechanically secured. Subsequently, the circuit board 8 is changed and restructured from the two-dimensional or developed form into the three-dimensional form shown in FIG. 3 by forming processes.

LIST OF REFERENCE NUMBERS

1 Sensor device
2 Plug-in housing
3 Cable
4 Housing section
5 Measurement window device
6a, b, c Plastic rings
7 Evaluation device
8 Printed circuit board
9 Transmitter platform
10 Receiver platform
11 Lubricant
12 Lubricant chamber
13 Measurement chamber
14 Diode device
15 Measurement radiation
16 Receiving device
17 Additional receiving device
18 Pin
19 not used
20 Passage opening
21 Diode contact position
22 DIE
23 Substrate
24 Diode area
25 Dome
26 Complete contact surface
27 Wire

The invention claimed is:

1. A sensor device for monitoring a lubricant state in a lubricant chamber, comprising:
   a transmitter platform, a plurality of diode devices as transmitter devices for a measurement radiation arranged on the transmitter platform, the transmitter platform is arranged in a measurement chamber,
   a measurement window device arranged between the measurement chamber and the lubricant chamber,
   a receiving device arranged in the measurement chamber longitudinally between the plurality of diode devices and the lubricant chamber, and the receiving device is configured to receive measurement radiation that is reflected from lubricant in the lubricant chamber,
   wherein at least one of the diode devices comprises a DIE, and
   a dome connected to the DIE by a contact surface that is arranged on a top side of the DIE with a light-emitting diode area.

2. The sensor device according to claim 1, wherein the dome is constructed as a drop on a horizontal surface or with a hemispherical shape, and a base surface of the dome forms the contact surface to the DIE.

3. The sensor device according to claim 1, wherein the DIE has a substrate with side surfaces, and the contact surface is bounded on the top side of the DIE.

4. The sensor device according to claim 1, wherein the dome is a plastic dome.

5. The sensor device according to claim 1, wherein the transmitter platform is constructed as a circuit board, the DIE is fixed on the circuit board, and connected electrically to the circuit board by wire bonds.

6. The sensor device according to claim 5, wherein connection areas of the wires for the wire bonds are arranged on the contact surface.

7. The sensor device according to claim 1, further comprising a cylindrical housing section, and the measurement chamber is constructed in an interior of the housing section and the measurement window device closes the housing section on a free end thereof.

8. The sensor device according to claim 7, wherein the housing section is part of a plug-in housing.

9. The sensor device according to claim 1, wherein a maximum diameter of the transmitter platform or an interior in an area of the transmitter platform is less than 10 mm.

10. The sensor device according to claim 1, wherein at least two diode devices each with one of the domes are arranged on the transmitter platform.

11. The sensor device according to claim 10, wherein the receiving device or another receiving device is arranged on the transmitter platform.

12. The sensor device according to claim 1, wherein the transmitter platform forms a partial area of a flexible circuit board.

13. A method for producing the sensor device according to claim 1, comprising in a first step, placing the DIE of the at least one diode device on the transmitter platform and in a subsequent step placing the dome is placed on the DIE.

14. The sensor device according to claim 1, further comprising an additional receiving device arranged in the measurement chamber that is configured as a reference detector.

15. The sensor device according to claim 14, wherein the additional receiving device is arranged on the transmitter platform.

16. The sensor device according to claim 14, wherein the additional receiving device is positioned between the plurality of diode devices.

17. The sensor device according to claim 1, wherein the receiving device is arranged on a receiver platform that is positioned longitudinally between the plurality of diode devices and the measurement window device.

* * * * *